US011015015B2

(12) United States Patent
Zhou et al.

(10) Patent No.: US 11,015,015 B2
(45) Date of Patent: May 25, 2021

(54) CO-PREPARATION OF POLYETHERAMINES AND ALKLYENE AMINES

(71) Applicant: Huntsman Petrochemical LLC, The Woodlands, TX (US)

(72) Inventors: Hui Zhou, The Woodlands, TX (US); Howard P Klein, Austin, TX (US); David C Lewis, Conroe, TX (US)

(73) Assignee: HUNTSMAN Petrochemical LLC, The Woodlands, TX (US)

(*) Notice: Subject to any disclaimer, the term of this patent is extended or adjusted under 35 U.S.C. 154(b) by 0 days.

(21) Appl. No.: 15/577,785

(22) PCT Filed: Nov. 30, 2016

(86) PCT No.: PCT/US2016/064052
§ 371 (c)(1),
(2) Date: Nov. 29, 2017

(87) PCT Pub. No.: WO2017/123333
PCT Pub. Date: Jul. 20, 2017

(65) Prior Publication Data
US 2018/0312624 A1    Nov. 1, 2018

Related U.S. Application Data

(60) Provisional application No. 62/277,522, filed on Jan. 12, 2016.

(51) Int. Cl.
| | | |
|---|---|---|
| *C07C 213/00* | (2006.01) |
| *C08G 18/50* | (2006.01) |
| *C08G 65/325* | (2006.01) |
| *C08G 65/322* | (2006.01) |
| *C08G 18/32* | (2006.01) |
| *C07C 213/02* | (2006.01) |
| *C08G 18/38* | (2006.01) |
| *C08G 18/66* | (2006.01) |
| *C08G 65/333* | (2006.01) |

(52) U.S. Cl.
CPC ........ *C08G 18/5021* (2013.01); *C07C 213/02* (2013.01); *C08G 18/3228* (2013.01); *C08G 18/3819* (2013.01); *C08G 18/5024* (2013.01); *C08G 18/6666* (2013.01); *C08G 65/322* (2013.01); *C08G 65/3255* (2013.01); *C08G 65/33303* (2013.01)

(58) Field of Classification Search
CPC .......... C07C 213/02; C08G 65/322; C08G 65/3255; C08G 65/33303; C08G 18/5021; C08G 18/3228; C08G 18/3819; C08G 18/5024
See application file for complete search history.

(56) References Cited

U.S. PATENT DOCUMENTS

| | | |
|---|---|---|
| 2,683,730 A | 7/1954 | Nelson et al. |
| 2,950,263 A | 8/1960 | Abbotson et al. |
| 3,012,008 A | 12/1961 | Lister |
| 3,152,998 A | 10/1964 | Moss |
| 3,344,162 A | 9/1967 | Rowton |
| 3,362,979 A | 1/1968 | Bentley |
| 3,394,164 A | 7/1968 | McClellan et al. |
| 3,654,370 A | 4/1972 | Yeakey |
| 4,014,933 A | 3/1977 | Boettger et al. |
| 4,152,353 A | 5/1979 | Habermann |
| 4,705,814 A | 11/1987 | Grigsby, Jr. et al. |
| 4,748,192 A | 5/1988 | Smith |
| 4,766,245 A | 8/1988 | Larkin et al. |
| 5,639,413 A | 6/1997 | Crivello |
| 5,972,563 A | 10/1999 | Steinmann et al. |
| 7,683,007 B2 | 3/2010 | Renken et al. |
| 9,067,865 B2 | 6/2015 | Klein et al. |
| 2009/0264652 A1* | 10/2009 | Kubanek .............. B01J 23/8926 544/177 |
| 2012/0071623 A1* | 3/2012 | Eling .................. C08G 18/5024 528/78 |
| 2017/0362164 A1* | 12/2017 | Wigbers ................ C07C 213/02 |

FOREIGN PATENT DOCUMENTS

| | | |
|---|---|---|
| WO | 2014154783 A1 | 10/2014 |
| WO | 2015058032 A1 | 4/2015 |
| WO | 2015069531 A1 | 5/2015 |

* cited by examiner

*Primary Examiner* — Michael L Leonard
(74) *Attorney, Agent, or Firm* — Huntsman Petrochemical LLC; Aleece M. Hayes

(57) ABSTRACT

The present disclosure provides a process for the co-preparation of a polyetheramine and an alkylene amine mixture by aminating a liquid polyol initiator mixture comprising an alkoxylated alcohol and a solid high melting polyol. The polyetheramine and alkylene amine mixture may be used in a variety of applications, such as a curing agent for epoxy resin formulations or as a raw material in the synthesis of polyurea.

8 Claims, No Drawings

CO-PREPARATION OF POLYETHERAMINES AND ALKLYENE AMINES

CROSS-REFERENCE TO RELATED APPLICATIONS

This application is the National Phase of International Application PCT/US2016/064052 filed Nov. 30, 2016 which designated the U.S. and which claims priority to U.S. App. Ser. No. 62/277,522 filed Jan. 12, 2016. The noted applications are incorporated herein by reference.

STATEMENT REGARDING FEDERALLY SPONSORED RESEARCH OR DEVELOPMENT

Not applicable.

FIELD OF THE INVENTION

The present disclosure provides a process for producing a polyetheramine and an alkylene amine mixture by aminating an alkoxylated alcohol and a high melting polyol. The amine mixture may be used in a variety of applications, such as, in the curing of an epoxy resin or in the synthesis of a polyurea.

BACKGROUND

The amination of alkoxylated alcohols is a process which has been long recognized in the prior art. It generally concerns the reaction of an alkoxylated alcohol with ammonia in the presence of a hydrogenation catalyst and usually in the presence of hydrogen. The polyetheramines which are subsequently produced find many uses, for example, as curing agents for epoxy resins or as raw materials in the synthesis of polyamides and polyureas.

The overall commercial process generally entails: the alkoxylation of initiator alcohols, such as propylene glycol or glycerin, by the addition of alkylene oxides, such as ethylene oxide, propylene oxide or butylene oxide, to form precursor polyols having various functionalities; and, subjecting the precursor polyols to reductive amination at high temperatures and pressures to produce the polyetheramines. In most instances, the initiator alcohols which are alkoxylated are either liquid at room temperature or a low melting point solid. Because of high energy consumption and the requirement of more capital investment to add heat tracing capability, higher melting point initiator alcohols are typically excluded from current processes. However, these high melting point initiator alcohols sometimes have unique and desirable features, such as, a rigid backbone, high functionality, etc. Thus, it would be advantageous to provide a process which can handle such high melting point initiator alcohols without having to implement major modifications to traditional manufacturing facilities.

SUMMARY

This application describes new processes for co-preparing a polyetheramine and an alkylene amine mixture. The processes utilize an alkoxylated alcohol as a solvent for and co-reactant with a high melting polyol in a reductive amination step. The polyetheramine and alkylene amine mixture may be combined with an epoxy resin to form an epoxy resin formulation or reacted with an organic polyisocyanate to form a polyurea.

DETAILED DESCRIPTION

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "an amine" means one amine or more than one amine. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment. If the specification states a component or feature "may", "can", "could", or "might" be included or have a characteristic, that particular component or feature is not required to be included or have the characteristic.

The term "substantially free" means, when used with reference to the substantial absence of a material, that such a material is present, if at all, as an incidental impurity or by-product. For instance in some embodiments, the material may be present at an amount of no more than 0.01 weight percent, or alternatively no more than 0.001 weight percent, based on the total weight of the system.

According to one aspect, the present disclosure provides a process for the co-preparation of a polyetheramine and an alkylene amine mixture. The process generally includes: (a) mixing and heating an alkoxylated alcohol initiator and a solid high melting polyol having from 2 to 8 hydroxyl groups per molecule to form a liquid polyol initiator mixture; and (b) charging the liquid polyol initiator mixture to a reductive amination zone and reductively aminating the mixture in the presence of a reductive amination catalyst and ammonia to form the polyetheramine and the alkylene amine mixture.

It has been surprisingly found that the alkoxylated alcohol initiator acts as both a solvent to dissolve the high melting polyol and as part of the reaction medium which is aminated. Thus, although the melting points of the high melting polyols under consideration may be relatively high, for example, in one embodiment at least about 100° C., in still other embodiments at least about 80° C., or at least about 60° C., or at least about 40° C. or even at least about 30° C., alkoxylated alcohol initiator and high melting polyol mixture will have a greatly reduced melting point allowing the process to amount to a single stage process in commercial practice.

Advantages to the process described herein are readily apparent. For instance, since the process employs a single stage, a significant reduction in the number of undesired by-products will be produced as compared to state of the art multi-stage processes. Furthermore, because the alkoxylated alcohol acts as a solvent, the process may be carried out substantially free of water or other solvent which can also contribute to impurities and undesired by-products.

According to one aspect of the present disclosure, the alkoxylated alcohol initiator is a polyoxyalkylene polyol formed from the adduction of an alcohol and an alkylene oxide. In one embodiment, the alcohol is a univalent alcohol, for example methanol, ethanol, propanol or butanol. In another embodiment, the alcohol is a polyvalent alcohol. The polyvalent alcohol may be a bivalent alcohol, such as ethylene glycol, propylene glycol, tripropylene glycol, neopentyl glycol, polytetramethylene ether glycol, 1,3-butanediol, 1,4-butanediol or 1,4-cyclohexanedimethanol, a tervalent alcohol, such as glycerin or trimethylolpropane, a quadrivalent alcohol, such as pentaerythritol, a sexivalent alcohol, such as sorbitol, or an octavalent alcohol, such as sucrose.

In another embodiment, the alkylene oxide may be ethylene oxide, propylene oxide, butylene oxide or a combination thereof. In one embodiment, the alkylene oxide is propylene oxide and/or ethylene oxide. When propylene oxide and ethylene oxide are used in combination, the adduct may be a block adduct or a random adduct.

In one particular embodiment, the alkoxylated polyol initiator is a compound having the formula (1)

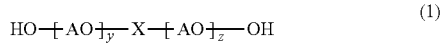

(1)

where each AO may be identical or different and each may be, independently of one another, ethyleneoxy, propyleneoxy, or butyleneoxy, y and z may each individually be a number from 0 to 6, for example, 0, 1, 2, 3, 4, 5 or 6, wherein at least one of y and z is 1 or more, y+z may be a number between 1 and 12, for example, 1, 2, 3, 4, 5, 6, 7, 8, 9, 10, 11, 12 and X may be a linear or branched $C_2$-$C_{18}$ alkylene, for example a $C_2$-$C_{12}$ alkylene and particularly a $C_2$-$C_6$ alkylene, or a $C_3$-$C_{12}$ cycloalkylene, for example a $C_4$-$C_8$ cycloalkylene and particularly a $C_5$-$C_8$ cycloalkylene, or a $C_2$-$C_4$ alkylene-$C_3$-$C_{12}$ cycloalkylene, for example a $C_2$-$C_4$ alkylene-$C_5$-$C_6$ cycloalkylene, or a $C_2$-$C_4$ alkylene-$C_3$-$C_{12}$ cycloalkylene-$C_2$-$C_4$ alkylene, for example a $C_2$-$C_4$ alkylene-$C_5$-$C_6$ cycloalkylene-$C_2$-$C_4$ alkylene.

According to another aspect, the high melting polyol is a compound having 2 to 8 hydroxyl groups, and in some embodiments 2 to 3 hydroxyl groups. In one embodiment, the high melting polyol may be: neopentyl glycol; pentaerythritol, which may be relatively pure or may contain varying amounts of dipentaerythritol and tripentaerythritol; dipentaerythritol; tripentaerythritol; the methyl alpha d-glucoside of corn starch; corn starch; sucrose; lactose; d-mannitol; anhydrous sorbitol; dulcitol; erythritol; threitol; arabinitol; xylitol; ribitol; allitol; altritol; gulitol; galactitol; talitol; maltitol; isomaltitol; lactitol; trimethylolpropane; trimethylolethane; inositol; glucose; fructose; and mixtures thereof. In one particular embodiment, the high melting polyol is a compound having a melting point of at least about 80° C., in other embodiments at least about 90° C., while in still other embodiments at least about 100° C. under atmospheric pressure.

The alkoxylated alcohol initiator and high melting polyol are mixed and heated to dissolve the high melting polyol and form a liquid polyol initiator mixture. In some embodiments, the weight ratio of the alkoxylated alcohol initiator to high melting polyol (i.e. alkoxylated alcohol initiator:high melting polyol) may be, for example, equal to or greater than the following ratios: 95:5; 90:10; 85:15; 80:20; 75:25; 70:30; 65:35; 60:40; 55:45; or 51:49. In other embodiments, the weight ratio of the high melting polyol to alkoxylated alcohol initiator (i.e. high melting polyol:alkoxylated alcohol initiator), may be, for example, equal to or greater than the following ratios: 95:5; 90:10; 85:15; 80:20; 75:25; 70:30; 65:35; 60:40; 55:45; or 51:49. In still another embodiment, the weight ratio of the high melting polyol to alkoxylated alcohol initiator (i.e. high melting polyol:alkoxylated alcohol initiator), may be, for example, equal to about 50:50. In one particular embodiment, the liquid polyol initiator mixture is substantially free of water and other solvents.

Mixing may occur by any means known, such as, via a propeller, stirring device or the like, in a vessel, or via an in-line static mixer whereby mixing may be accomplished within a conduit. The mixture is then heated to facilitate dissolving of the high melting polyol. In one embodiment, the mixture is heated at a temperature of at least about 40° C., in other embodiments at least about 60° C., in still other embodiments at least about 70° C., and in still other embodiments at least about 80° C. In other embodiments, the mixture may be heated at a temperature within the range of about 50° C. to about 150° C. In some aspects, the liquid polyol initiator mixture, after mixing and heating, may optionally be neutralized with any suitable acid or chemical adsorbent, such as for example, oxalic acid or magnesium silicate, and filtered for the removal of any insoluble materials present.

The liquid polyol initiator mixture is then charged to a reductive amination zone and reductively aminated in the presence of a reductive amination catalyst and ammonia to form the polyetheramine and alkylene amine mixture. The reactants may be fed as a stream, typically continuously, to a fixed bed of the reductive amination catalyst. The solid catalyst is usually in the form of pellets, tablets, extrudates, spheres, etc. The active catalyst components can either be unsupported or deposited on a support material, as is known to those skilled in the art, such as alumina, silica, etc. The reaction occurs in the bed and thus the bed defines the reaction zone. The effluent from the bed or the reaction zone is also a stream comprising the unreacted components of the feed stream and the principal polyetheramine and alkylene amine reaction products, plus a number of other amine compounds.

In some embodiments, the reductive amination process conditions may include, for example, a temperature within the range of about 100° C. to about 240° C. and a pressure within the range of about 500 psi to about 5,000 psi with temperatures within the range of about 180° C. to about 220° C. and pressures within the range of about 1,000 psi to about 2,500 psi being preferred in some embodiments. The effluent may be depressured so as to recover excess hydrogen and ammonia for recycle and then fractionated to remove byproduct water of reaction and to provide the desired polyetheramine and alkylene amine mixture.

Any suitable hydrogenation catalyst may be used during reductive amination, such as those described in U.S. Pat. No. 3,654,370, the contents of which are incorporated herein by reference. In some embodiments, the hydrogenation catalyst may comprise one or more of the metals of group VIIIB of the Periodic Table, such as iron, cobalt, nickel, ruthenium, rhodium, palladium, and platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 mole percent to about 85 mole percent of nickel, about 14 mole percent to about 37 mole percent of copper and about 1 mole percent to about 5 mole percent of chromium (as chromia), such as a catalyst of the type disclosed in U.S. Pat. No. 3,152,998. As another example, a catalyst of the type disclosed in U.S. Pat. No. 4,014,933 may be used containing from about 70% by weight to about 95% by weight of a mixture of cobalt and nickel and from about 5% by weight to about 30% by weight of iron. As still another example, a catalyst of the type disclosed in U.S. Pat. No. 4,152,353 may be used, comprising nickel, copper and a third component which may be iron, zinc, zirconium or a mixture thereof, for example, a catalyst containing from about 20% by weight to about 49% by weight of nickel, about 36% by weight to about 79% by weight of copper and about 1% by weight to about 15%) by weight of iron, zinc, zirconium or a mixture thereof. In still another example, a catalyst of the type described in U.S. Pat. No. 4,766,245 may be used comprising about 60% by weight to about 75% by weight of nickel and about 25% by weight to about 40% by weight of aluminum. In yet another example, a catalyst of the type described in U.S. Pat. No. 7,683,007 may be used comprising nickel, copper, zirconium and/or chromium, oxygen, and tin.

In conducting the reductive amination, the reductive amination conditions to be utilized may suitably include the use of from about 4 moles to about 150 moles of ammonia per hydroxyl equivalent of polyol initiator feedstock. Hydrogen is preferably used in an amount ranging from about 0.5 mole equivalents to about 10 mole equivalents of hydrogen per hydroxyl equivalent of polyol initiator feedstock. The contact times within the reaction zone, when the reaction is conducted on a batch basis, may suitably be within the range of from about 0.1 hours to about 6 hours and more preferably from about 0.15 hours to about 2 hours.

When the reaction is conducted on a continuous basis using catalyst pellets, reaction rates may suitably be from about 0.1 grams to about 2 grams of feedstock per hour per cubic centimeter of catalyst and, more preferably, from about 0.3 grams to about 1.6 grams of feedstock per hour per cubic centimeter of catalyst.

According to another aspect, the present disclosure provides a mixture comprising a polyetheramine and an alkylene amine formed from the process described above.

Due to its favorable properties, the polyetheramine and alkylene amine mixture described herein may be used as a constituent in a formulation which finds use in a wide variety of industrial applications, for example in the production of moldings (casting resins), fiber-reinforced composites, such as wind turbine generator blades, for tool manufacture or for the production of coatings and/or intermediate coatings on a wide variety of substrates, for example on substrates of an organic or inorganic nature, such as wood, wood fibers (wood sealing), textiles of natural or synthetic origin, plastics, glass, ceramics, building materials, such as concrete, fiberboard, and artificial stone, on metal, such as iron, aluminum, copper and the like. In addition, the polyetheramine and alkylene amine mixture described herein can be employed as a constituent of adhesives, cement, laminating resin, synthetic resin cement, paint or coating. The formulation can be prepared prior to or during use by contacting the constituents, for example by mixing, and it can also be applied to any type of surface(s), for example, by brushing, spraying, dipping coating, extruding, printing, electrostatic spraying, and the like, and then subsequently cured to form a cured material.

According to one aspect, the polyetheramine and alkylene amine mixture of the present disclosure can be combined with an epoxy resin to form an epoxy resin formulation. The epoxy resin formulation may then be subjected to conditions sufficient to cause the epoxy resin formulation to cure and form a cured product.

The epoxy resin may be any one or mixture of reactive epoxy resin(s) having a 1,2-epoxy equivalency (functionality), on the average, of at least 1 epoxide groups per molecule, preferably at least 1.3 epoxide groups per molecule, and more preferably at least 1.6 epoxide groups per molecule, and even more preferably with epoxy resins having a functionality of at least 2 epoxy groups per molecule such that the mixture will polymerize to form a useful material with the polyetheramine and alkylene amine mixture described herein or its blend with other amine hardeners. In another aspect, the epoxy resin has a functionality on the average ranging from at least 1.3 epoxide groups per molecule to about 8 epoxide groups per molecule, preferably from at least about 1.6 epoxide groups per molecule to about 5 epoxide groups per molecule. The epoxy resin can be saturated or unsaturated, linear or branched, aliphatic, cycloaliphatic, aromatic or heterocyclic, and may bear substituents such as bromine or fluorine. It may be monomeric or polymeric, liquid or solid, but is preferably liquid or a low melting solid at room temperature.

According to one aspect, the epoxy resin is a polyglycidyl epoxy compound, such as a polyglycidyl ether, poly(β-methylglycidyl) ether, polyglycidyl ester or poly(β-methylglycidyl) ester. The synthesis and examples of polyglycidyl ethers, poly(β-methylglycidyl) ethers, polyglycidyl esters and poly(β-methylglycidyl) esters are disclosed in U.S. Pat. No. 5,972,563, which is incorporated herein by reference. For example, ethers may be obtained by reacting a compound having at least one free alcoholic hydroxyl group and/or phenolic hydroxyl group with a suitably substituted epichlorohydrin under alkaline conditions or in the presence of an acidic catalyst followed by alkali treatment. The alcohols may be, for example, acyclic alcohols, such as ethylene glycol, diethylene glycol and higher poly(oxyethylene) glycols, propane-1,2-diol, or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol-1,1,1-trimethylolpropane, bistrimethylolpropane, pentaerythritol and sorbitol. Suitable glycidyl ethers may also be obtained, however, from cycloaliphatic alcohols, such as 1,3- or 1,4-dihydroxycyclohexane, bis(4-hydroxycyclo-hexyl)methane, 2,2-bis(4-hydroxycyclohexyl)propane or 1,1-bis(hydroxymethyl)cyclohex-3-ene, or they may possess aromatic rings, such as N,N-bis(2-hydroxyethyl)aniline or p,p'-bis(2-hydroxyethylamino) diphenylmethane.

Representative examples of polyglycidyl ethers or poly (β-methylglycidyl) ethers include those based on monocyclic phenols, for example, on resorcinol or hydroquinone, on polycyclic phenols, for example, on bis(4-hydroxyphenyl) methane (Bisphenol F), 2,2-bis(4-hydroxyphenyl)propane (Bisphenol A), bis(4-hydroxyphenyl)S (Bisphenol S), alkoxylated Bisphenol A, F or S, trial extended Bisphenol A, F or S and brominated Bisphenols A, F or S, hydrogenated Bisphenol A, F or S, glycidyl ethers of phenols and phenols with pendant groups or chains, on condensation products, obtained under acidic conditions, of phenols or cresols with formaldehyde, such as phenol novolacs and cresol novolacs, or on siloxane diglycidyls.

Polyglycidyl esters and poly(β-methylglycidyl) esters may be produced by reacting epichlorohydrin or glycerol dichlorohydrin or β-methylepichlorohydrin with a polycarboxylic acid compound. The reaction is expediently carried out in the presence of bases. The polycarboxylic acid compounds may be, for example, glutaric acid, adipic acid, pimelic acid, suberic acid, azelaic acid, sebacic acid or dimerized or trimerized linoleic acid. Likewise, however, it is also possible to employ cycloaliphatic polycarboxylic acids, for example tetrahydrophthalic acid, 4-methyltetrahydrophthalic acid, hexahydrophthalic acid or 4-methylhexahydrophthalic acid. It is also possible to use aromatic polycarboxylic acids such as, for example, phthalic acid, isophthalic acid, trimellitic acid or pyromellitic acid, or else carboxyl-terminated adducts, for example of trimellitic acid and polyols, for example glycerol or 2,2-bis(4-hydroxycyclohexyl)propane, can be used.

In another aspect, the epoxy resin is a non-glycidyl epoxy compound. Non-glycidyl epoxy compounds may be linear, branched, or cyclic in structure. For example, there may be included one or more epoxide compounds in which the epoxide groups form part of an alicyclic or heterocyclic ring system. Others include an epoxy-containing compound with at least one epoxycyclohexyl group that is bonded directly or indirectly to a group containing at least one silicon atom. Examples are disclosed in U.S. Pat. No. 5,639,413, which is incorporated herein by reference. Still others include epoxides which contain one or more cyclohexene oxide groups and epoxides which contain one or more cyclopentene oxide groups. Particularly suitable non-glycidyl epoxy compound's include the following difunctional non-glycidyl epoxide compounds in which the epoxide groups form part of an alicyclic or heterocyclic ring system: bis(2,3-epoxycyclopentyl) ether, 1,2-bis(2,3-epoxycyclopentyloxy)ethane, 3,4-epoxycyclohexyl-methyl, 3,4-epoxycyclohexanecarboxylate, 3,4-epoxy-6-methyl-cyclohexylmethyl 3,4-epoxy-6-methylcyclohexanecarboxylate, di(3,4-epoxycyclohexylmethyl)hexanedioate, di(3,4-epoxy-6-methylcyclohexylmethyl) hexanedioate, ethylenebis(3,4-epoxycyclohexanecarboxylate), ethanediol di(3,4-epoxycyclohexylmethyl)ether, vinylcyclohexene dioxide, dicyclopentadiene diepoxide or 2-(3,4-epoxycyclohexyl-5, 5-spiro-3,4-epoxy)cyclohexane-1,3-dioxane, and 2,2'-bis-(3,4-epoxy-cyclohexyl)-propane.

In another implementation, the epoxy resin is an epoxy novolac compound obtained by the reaction of, preferably in the presence of a basic catalyst such as sodium or potassium hydroxide, an epihalohydrin, such as epichlorohydrin, with a resinous condensate of an aldehyde, such as formaldehyde and either a monohydric phenol or polyhydric phenol.

In other implementations, the epoxy resin is a poly(N-glycidyl) compound or poly(S-glycidyl) compound. Poly(N-glycidyl) compounds are obtainable, for example, by dehydrochlorination of the reaction products of epichlorohydrin with amines containing at least two amine hydrogen atoms. These amines may be, for example, n-butylamine, aniline, toluidine, m-xylenediamine, bis(4-aminophenyl)methane or bis(4-methylaminophenyl)methane. Other examples of poly (N-glycidyl) compounds include N,N'-diglycidyl derivatives of cycloalkyleneureas, such as ethyleneurea or 1,3-propyleneurea, and N,N'-diglycidyl derivatives of hydantoins, such as of 5,5-dimethylhydantoin. Examples of poly(S-glycidyl) compounds are di-S-glycidyl derivatives derived from dithiols, for example ethane-1,2-dithiol or bis(4-mercaptomethylphenyl) ether.

It is also possible to employ epoxy-containing compounds in which the 1,2-epoxide groups are attached to different heteroatoms or functional groups. Examples of these compounds include the N,N,O-triglycidyl derivative of 4-aminophenol, the glycidyl ether/glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Other epoxide derivatives may be employed, such as vinyl cyclohexene dioxide, limonene dioxide, limonene monoxide, vinyl cyclohexene monoxide, 3,4-epoxycyclohexylmethyl acrylate, 3,4-epoxy-6-methyl cyclohexylmethyl 9,10-epoxystearate, and 1,2-bis(2,3-epoxy-2-methylpropoxy)ethane. Also conceivable is the use of oxetanes or liquid pre-reacted adducts of epoxy-containing compounds, such as those mentioned above, with hardeners for the epoxy resins.

The epoxy resin formulation may further contain customary additives and auxiliaries such as stabilizers, modifiers, antifoaming agents, toughening agents, accelerators, co-curing agents, leveling agents, thickening agents, flame retardants, antioxidants, pigments, dyes, fillers, and combinations thereof. For example, an accelerator such as guanidine or a derivative thereof may be used in the epoxy resin formulation. Examples of guanidine derivatives include without limitation, an alkylguanidine such as dimethylguanidine or tetramethyl guanidine, or a guanidinium salt derived from any of these. Examples of guanidinium salts include without limitation, guanidine carbonates, guanidine acetates, and guanidine nitrates. One skilled in the art with the benefit of this disclosure will recognize appropriate additives and auxiliaries for use in the implementations described herein.

Once formulated, the epoxy resin formulation may be applied to one or more surfaces, for example, by brushing, spraying, dipping, electrostatic spraying, etc., and subjected to conditions suitable to cause the epoxy resin system to cure. In one aspect, the epoxy resin formulation is cured at ambient conditions. In another aspect, the epoxy resin formulation is cured at an elevated temperature such as, at a temperature within the range from about 40° C. to about 220° C. In some aspects of the present disclosure, a lower cure temperature and/or lower cure time may be needed to reach desired cure properties, such as glass transition temperatures, than is typically required in current epoxy resin systems. Achieving improved cure property development at lower curing (such as baking) temperatures and/or shorter curing times means a potential savings in energy costs and a possible reduction in manufacturing process time (increased productivity). In aspects of the present disclosure, the temperature used in curing may be about, or less than, 40° C., 45° C., 50° C., 55° C., 60° C. and 65° C. In implementations of the present disclosure, the cure time may be from about 2 hours (hrs) to about 6 hrs, including the intervals of about 2.5 hrs, 3 hrs, 3.5 hrs, 4 hrs, 4.5 hrs, 5 hrs and 5.5 hrs. In an implementation of the present disclosure, the epoxy resin system is cured from about 3 to about 6 hours at about 55° C. One skilled in the art will recognize, with the benefit of this disclosure, how to reach desired cure properties using lower temperatures and/or lower cure times.

In still another implementation, the polyetheramine and alkylene amine mixture of the present disclosure is reacted with an organic polyisocyanate to form a polyurea. The organic polyisocyanate includes standard isocyanate compounds and compositions known to those skilled in the art. Examples include MDI-based quasi prepolymers such as those commercially available as RUBINATE®9480, RUBINATE®9484, and RUBINATE®9495 brand products which are all available from Huntsman International, LLC. Liquefied MDI such as MONDUR® ML isocyanate, available from Bayer Material Science, may also be used as all or part of the isocyanate.

Other organic polyisocyanates which can be employed include those generally known to one skilled in the art. Thus, for instance, they can include aliphatic isocyanates of the type described in U.S. Pat. No. 4,748,192. Accordingly, they are typically aliphatic diisocyanates and, more particularly, are the trimerized or the biuretic form of an aliphatic diisocyanate, such as hexamethylene diisocyanate, or the bifunctional monomer of the tetra alkyl xylene diisocyanate, such as the tetramethyl xylene diisocyanate. Another example of an aliphatic isocyanate is cyclohexane diisocyanate. Other useful aliphatic isocyanates are described in U.S. Pat. No. 4,705,814 which is fully incorporated herein by reference. They include aliphatic diisocyanates, for example, alkylene diisocyanates with 4 to 12 carbon atoms in the alkylene group, such as 1,12-dodecane diisocyanate and 1,4-tetramethylene diisocyanate. Also described are cycloaliphatic diisocyanates, such as 1,3 and 1,4-cyclohexane diisocyanate as well as any desired mixture of these isomers, 1-isocyanato-3,3,5-trimethyl-5-isocyanato methyl-cyclohexane (isophorone diisocyanate); 4,4'-,2,2'- and 2,4'-dicyclohexylmethane diisocyanate as well as the corresponding isomer mixtures, and the like.

A wide variety of aromatic polyisocyanates may also be used to form the polyurea of the present disclosure. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-iso-cyanatophenyl)methane, bis(3-methyl-4-isocyanatophenyl)methane, and 4,4'-diphenylpropane diisocyanate. Other aromatic polyisocyanates which may be used are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979, all of which are fully incorporated herein by reference. Usually, methylene-bridged polyphenyl polyisocyanate mixtures contain about 20 to about 100 weight percent methylene diphenyl diisocyanate isomers, with the remainder being polymethylene polyphenyl diisocyanates having higher functionalities and higher molecular weights. Typical of these are polyphenyl polyisocyanate mixtures containing about 20 to about 100 weight percent diphenyl diisocyanate isomers, of which about 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979. A preferred aromatic polyisocyanate is methylene bis (4-phenylisocyanate) or "MDI". Pure MDI, quasi-prepolymers of MDI, modified pure MDI, etc. are useful to prepare a polyurea according to the invention. Since pure MDI is a solid and, thus, often inconvenient to use, liquid products based on MDI or methylene bis(4-phenylisocyanate) are used herein. U.S. Pat. No. 3,394,164, incorporated herein by reference, describes a liquid MI product. More generally, uretonimine modified pure MDI is included also. This product is made by heating pure distilled MDI in the presence of a catalyst. The liquid product is a mixture of pure MDI and modified MDI. The term organic polyisocyanate also includes quasi-prepolymers of isocyanates or polyisocyanates with active hydrogen containing materials.

EXAMPLES

Example 1

2177 grams of neopentyl glycol and 5080 grams of Polyol R2490 were added to a dry, nitrogen purged reactor and the reactor was heated to about 80° C. with agitation. The temperature was then held at 80° C. until all of the neopentyl glycol had dissolved forming a clear solution. The resulting mixture remained homogeneous at room temperature.

Example 2

1234 grams of neopentyl glycol and 6024 grams of Polyol R2490 were added to a dry, nitrogen purged reactor and the reactor was heated to about 80° C. with agitation. The temperature was then held at 80° C. until all of the neopentyl glycol had dissolved forming a clear solution. The resulting mixture remained homogeneous at room temperature.

Example 3

1452 grams of neopentyl glycol and 5806 grams of PPG-230 were added to a dry, nitrogen purged reactor and the reactor was heated to about 80° C. with agitation. The temperature was then held at 80° C. until all of the neopentyl glycol had dissolved forming a clear solution. The resulting mixture remained homogeneous at room temperature.

Example 4

The mixtures of Examples 1-3 were aminated by adding ammonia and hydrogen to the corresponding mixtures of Examples 1-3 in a 100 cc continuous unit with a reductive amination catalyst. The mixtures of Examples 1-3 and ammonia were pumped separately and mixed in-line with hydrogen and then fed through the reductive amination catalyst bed. The mixtures of Examples 1-3 and ammonia were maintained at a 1:1 wt. feed ratio, while the ammonia to hydrogen mole ratio was maintained at about 10-20:1. The reactor pressure was maintained at 2000 psig and the temperature was maintained at about 180°-220° C. The mixtures of Examples 1-3 and ammonia feed rates varied between about 65 g/hr to about 100 g/hr. The resulting polyetheramine and alkylene amine mixtures were collected and stripped of excess ammonia, water and light amines to form the final polyetheramine and alkylene amine mixture.

While the foregoing is directed to embodiments of the present disclosure, other and further embodiments of the disclosure may be devised without departing from the basic scope thereof, and the scope thereof is determined by the claims that follow.

What is claimed is:

1. A process for the co-preparation of a polyetheramine and an alkylene amine mixture comprising (a) mixing and heating at a temperature of at least 40° C. an alkoxylated alcohol initiator and at least one solid high melting polyol having from 2 to 8 hydroxyl groups per molecule at a weight ratio of the solid high melting polyol to alkoxylated alcohol initiator equal to or greater than 51:49 to form a liquid polyol initiator mixture; and (b) charging the liquid polyol initiator mixture to a reductive amination zone and reductively aminating the liquid polyol initiator mixture in the presence of a reductive amination catalyst and ammonia to form the polyetheramine and the alkylene amine mixture wherein the high melting polyol is neopentyl glycol; pentaerythritol; dipentaerythritol; tripentaerythritol; a methyl alpha d-glucoside of corn starch; corn starch; sucrose; lactose; d-mannitol; anhydrous sorbitol; dulcitol; erythritol; threitol; arabinitol; xylitol; ribitol; allitol; altritol; gulitol; galactitol; talitol; maltitol, isomaltitol; lactitol; trimethylolpropane; trimethylolethane; inositol; glucose; fructose; and mixtures thereof.

2. The process of claim 1, wherein the alkoxylated alcohol initiator is a polyoxyalkylene polyol formed from the adduction of an alcohol and an alkylene oxide.

3. The process of claim 2, wherein the alcohol is ethylene glycol, propylene glycol, tripropylene glycol, neopentyl glycol, polytetramethylene ether glycol, 1,3-butanediol, 1,4-butanediol or 1,4-cyclohexanedimethanol.

4. The process of claim 1, wherein the liquid polyol initiator mixture is substantially free of water and solvent.

5. A polyetheramine and an alkylene amine mixture obtained by: (a) mixing and heating at a temperature of at least 40° C. an alkoxylated alcohol initiator and at least one solid high melting polyol having from 2 to 8 hydroxyl groups per molecule at a weight ratio of the solid high melting polyol to the alkoxylated alcohol initiator equal to or greater than 51:49 to form a liquid polyol initiator mixture; and (b) charging the liquid polyol initiator mixture to a reductive amination zone and reductively aminating the liquid polyol initiator mixture in the presence of a reductive amination catalyst and ammonia to form the polyetheramine and the alkylene amine mixture wherein the high melting polyol is neopentyl glycol; pentaerythritol; dipentaerythritol; tripentaerythritol; a methyl alpha d-glucoside of corn starch; corn starch; sucrose; lactose; d-mannitol; anhydrous sorbitol; dulcitol; erythritol; threitol; arabinitol; xylitol; ribitol; allitol; altritol; gulitol; galactitol; talitol; maltitol, isomaltitol; lactitol; trimethylolpropane; trimethylolethane; inositol; glucose; fructose; and mixtures thereof.

6. An epoxy resin formulation comprising an epoxy resin and the polyetheramine and alkylene amine mixture of claim 5.

7. A process for forming a polyurea comprising reacting the polyetheramine and alkylene amine mixture of claim 5 with an organic polyisocyanate.

8. A polyurea produced by the process of claim 7.

* * * * *